United States Patent [19]

Molnar et al.

[11] Patent Number: 5,053,404
[45] Date of Patent: Oct. 1, 1991

[54] NOVEL STEROID DERIVATIVES, PHARMACEUTICAL COMPOSITIONS CONTAINING THEM AND PROCESS FOR PREPARING SAME

[75] Inventors: Csaba Molnar; György Hajos; Laszlo Szporny; Jozsef Toth; Arpad Kiraly; Anna Boor nee Mezei; Janos Csörgei; Kristina Szekely; Lilla Forgacs; György Fekete; Bulcsu Herenyi; Sandor Holly; Jozsef Szunyog, all of Budapest, Hungary

[73] Assignee: Richter Gedeon Vegyeszeti Gyar R. T., Budapest, Hungary

[21] Appl. No.: 491,682

[22] Filed: Mar. 9, 1990

[30] Foreign Application Priority Data

Mar. 9, 1989 [HU] Hungary .............................. 1155/89

[51] Int. Cl.$^5$ ............................................. C07J 71/00
[52] U.S. Cl. ........................................ 514/174; 540/27; 540/63; 540/69; 540/70; 549/437; 549/449
[58] Field of Search ................... 514/174; 540/63, 100, 540/27, 69, 70; 549/449, 437

[56] References Cited

U.S. PATENT DOCUMENTS

| | | | |
|---|---|---|---|
| 3,167,545 | 1/1965 | Rosenkranz et al. | 540/63 |
| 3,345,362 | 10/1987 | Rapala | 540/63 |
| 3,798,216 | 3/1974 | Boissier et al. | 540/70 |
| 3,929,768 | 12/1975 | Brattsand et al. | 514/178 |
| 3,992,534 | 11/1976 | Brattsan et al. | 540/63 |

OTHER PUBLICATIONS

Fried, et al., JACS, vol. 80, 1958, pp. 2338-2339.
Bernstein et al., JACS 81, 1959, pp. 1689 to 1696.
Allen et al., JACS vol. 78, 1956, pp. 1909-1913.
Lepetit, Chemical Abstracts vol. 63, 1965 Abstract 14786.
Kurbanov, et al., Izu. Akad. Nauk Turkmssr Spr. Fiz-Tpkh Khim Geol. Nauk 1989(2).

110-12 Chemical Abstracts vol. 111, 1989, Abstract 194644S.
Merck Index, 10th Edition, Compound 1435.
J.A.C.S., 95, No. 9, 2865-2868 (1973).
Acta Cryst, 834 3027-3036 (1978).
J. Chem. Soc., pp. 4383-4388 (1955).
International Synposion on Molecular Recognition, its role in Chemistry and Biochemistry, SOPRON (1988).

Primary Examiner—Mukund J. Shah
Assistant Examiner—E. C. Ward
Attorney, Agent, or Firm—Herbert Dubno; Jonathan Myers

[57] ABSTRACT

The invention relates to antiinflammatory compounds of the formula (I),

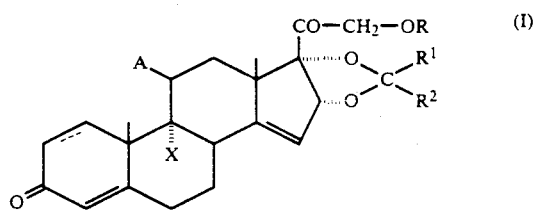

wherein
  A stands for hydrogen or hydroxyl group;
  X stands for hydrogen or halogen with the proviso that if A is hydrogen, then X also means hydrogen;
  R stands for hydrogen, benzoyl or $C_{1-8}$alkanoyl group;
  $R^1$ and $R^2$, which are the same or different, stand for hydrogen or a $C_{1-4}$alkyl group; or one of $R^1$ and $R^2$ is hydrogen and the other is phenyl group; or $R^1$ and $R^2$ together form a $C_{4-5}$alkylene group;
  means a single or double bond between two adjacent carbon atoms, as well as pharmaceutical compositions containing these compounds and a process for their preparation.

6 Claims, No Drawings

NOVEL STEROID DERIVATIVES, PHARMACEUTICAL COMPOSITIONS CONTAINING THEM AND PROCESS FOR PREPARING SAME

The invention relates to novel $\Delta^{14}$-16α,17-dihydroxypregnane-16,17-cyclic aldehyde acetal and -cyclic ketone ketal derivatives of formula (I),

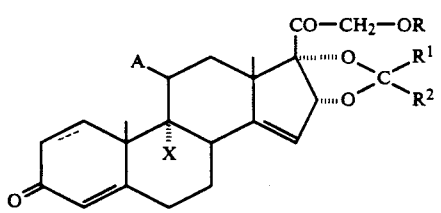

wherein

A stands for hydrogen or hydroxyl group;

X stands for hydrogen or halogen with the proviso that if A is hydrogen, then X also means hydrogen;

R stands for hydrogen, benzoyl or a $C_{1-8}$alkanoyl group;

$R^1$ and $R^2$, which are the same or different, stand for hydrogen or a $C_{1-4}$alkyl group; or one of $R^1$ and $R^2$ is hydrogen and the other is a phenyl group; or $R^1$ and $R^2$ together form a $C_{4-5}$alkylene group;

--- means a single or double bond between two adjacent carbon atoms, and pharmaceutical compositions containing a physiologically effective dose of these compounds and a process for preparing these compounds and compositions. Furthermore, the invention relates to a method of treatment, which comprises using these compounds or compositions.

The steroid derivatives according to the invention possess highly effective antiinflammatory properties and therefore they can be used as active ingredients in antiinflammatory compositions.

As used herein: halogen means fluorine, chlorine, bromine or iodine, preferably fluorine or chlorine; $C_{1-8}$alkanoyl means formyl, acetyl, propionyl or any of the various butyryl, valeryl, hexanoyl, heptanoyl or octanoyl groups; in addition to the above groups, acyl involves benzoyl group, too. $C_{2-4}$alkanoic acids mean acetic, propionic, n- and isobutyric acid.

It was shown by biological investigations carried out as early as the 1950's [J. Am. Chem. Soc. 78, 1909 (1956)] that 16α-hydroxycorticoids have the same or higher antiinflammatory effects in comparison with those of the native adrenal cortex hormones, e.g. hydrocortisone whereas their harmful sodium-retaining (mineralocorticoid) action influencing the electrolyte balance of the organism is practically negligible [J. Am. Chem. Soc. 81, 1689 (1959)].

The antiinflammatory effect of the corticoid 16α,17-cyclic aldehyde acetals formed from 16α,17-dihydroxycorticoids is even higher than that of the mother compounds [U.S. Pat. No. 3,197,468; and J. Am. Chem. Soc. 80, 2338 (1958)]. One of these is (22RS)-11β,21-dihydroxy-16α,17-butylidenedioxypregna-1,4-dien-3,20-dione (hereinafter: budesonide) a drug used in therapeutical practice [Arzneim.-Forsch. 29, 1687 (1979)].

Although a number of 16,17-cyclic aldehyde acetals and -cyclic ketone ketals became known in the literature over the course of many years, no $\Delta^{14}$-pregnane derivative has been described.

According to the literature, steroidal 16,17-cyclic aldehyde acetals or ketone ketals can be prepared by reacting the corresponding 16,17-dihydroxycorticoid derivatives with an aldehyde or ketone, respectively, in the presence of an acid catalyst. [German Patent Specification (DE-PS) No. 1,131,213 and published German patent Application (DE-OS) No. 1,118,779; British Patent Specifications Nos. 916,996 and 933,867; U.S. Pat. Nos. 3,197,469 and 3,798,216; as well as Hungarian Patent Specification No. 166,680]. This reaction is carried out in the presence of a solvent or in an excess of the oxo compound used as reactant.

According to the Hungarian Patent Specification No. 195,519 cyclic orthoesters of the corresponding 16,17-dihydroxycorticoid derivatives are reacted with oxo compounds.

According to an other aspect of the invention, there is provided a process for the preparation of the new compounds of formula (I), which comprises a) reacting a $\Delta^{14}$-16α,17-dihydroxypregnane derivative of formula (II).

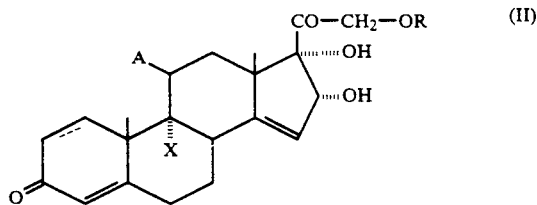

wherein A, X, R and the symbol (bond line) --- are as defined above, with an oxo compound of formula (IV),

wherein $R^1$ and $R^2$ are as defined above, in the presence of an acid catalyst;

b) reacting a $\Delta^{14}$-16α,17-dihydroxypregnane cyclic orthoester derivative of formula (III),

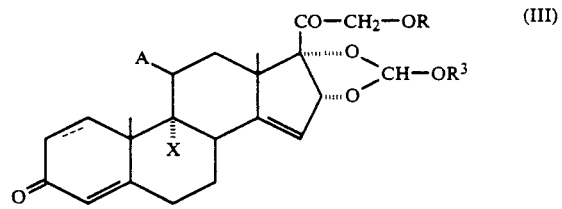

wherein A, X, R and the symbol (bond line) --- are as defined above and $R^3$ stands for a methyl or ethyl group, with an oxo compound of formula (IV),

wherein $R^1$ and $R^2$ are as defined above, in the presence of an acid catalyst, then, if desired, hydrolyzing the $\Delta^{14}$-16α,17-dihydroxy-pregnane-16,17-cyclic aldehyde acetal or -cyclic ketone ketal derivatives, respectively, of formula (I),

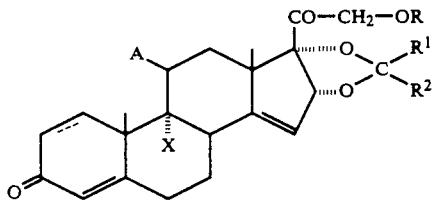

wherein A, X, $R^1$, $R^2$ and the symbol (bond line) --- are as defined above, obtained in process a) or b), and R is acyl to obtain $\Delta^{14}$-16α,17-dihydroxypregnane-16,17-cyclic aldehyde acetals or -cyclic ketone ketals containing hydrogen as R; and/or, if desired, acylating the thus obtained compounds of formula (I), wherein R means hydrogen to obtain compounds of formula (I),

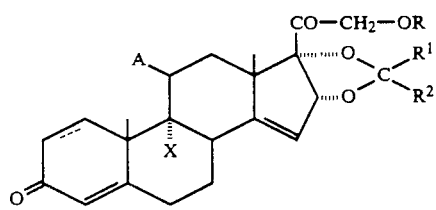

wherein R represents an acyl group.

The $\Delta^{14}$-16α,17-dihydroxypregnane derivatives of formula (II)

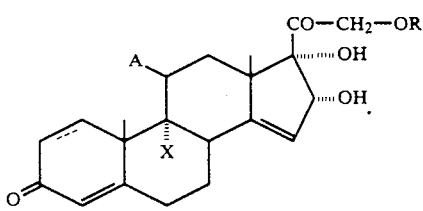

used as starting substances in the process according to the present invention can be prepared by the permanganate oxidation of the corresponding $\Delta^{16}$-pregnane derivatives by using the process described in our Hungarian patent application paralelly filed under No. 1156/89. The $\Delta^{14}$-16α,17-dihydroxypregnane cyclic orthosester derivatives of formula (III)

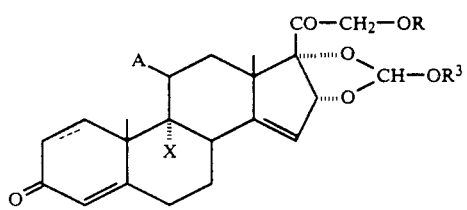

can be prepared analoguously as described in the Hungarian patent specification No. 195,519. The oxo compounds of the formula (IV)

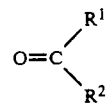

used as reactants are known and commercially available ketones and aldehydes.

According to a practical embodiment of process a) of the invention the corresponding oxo compound of formula (IV) is dissolved in a polar or apolar aprotic solvent. Benzene, tetrahydrofuran, dioxan, ethyl acetate, dichloromethane or acetonitrile and the like may be used for this purpose. An acid catalyst is added to the oxo compound of formula (IV) dissolved in any of the selected solvents or in a mixture thereof. Suitable acid catalysts are e.g. sulfuric, hydrochloric, perchloric, p-toluene-sulfonic or methanesulfonic acid or an organic acid such as trifluoroacetic acid. The temperature of the reaction mixture is suitably maintained between 10° C. and 40° C. during the addition and in the course of the reaction. To the reactant prepared as described above, the $\Delta^{14}$-16α,17-dihydroxypregnane derivatives of formula (II) to be transformed are added in a solid form or dissolved suitably in a solvent used for the preparation of the above reactant. The course of the reaction can be followed by thin layer chromatography (TLC). The formation of the cyclic acetal or ketal usually proceeds within 5 to 120 minutes. After termination of the reaction the mixture is suitably worked up in such a way that aqueous alkaline metal carbonate or hydrogen carbonate solution is added to the reaction mixture in order to neutralize the acid employed as catalyst. The system thus obtained is extracted with a water-immiscible solvent such as ethyl acetate or dichloromethane and after drying the solvent phase and evaporation, the product obtained is recrystallized.

Process b) according to the invention is essentially carried out in the same way as described in process a) apart from the starting substances.

When it is desired to prepare a derivative containing hydrogen as R from the thus obtained pregnane derivative of formula (I) containing an acyl group as R, the acyl group can be removed by hydrolysis. This reaction is suitably carried out in such a way that the acyl derivative obtained in the ketal forming reaction is dissolved in a protic water-miscible solvent, suitably in methanol and hydrolyzed by using an aqueous acid or alkali. It is suitable to carry out the hydrolysis by employing acid catalysis; aqueous perchloric acid is preferably used for this purpose. The hydrolysis of derivatives containing benzoyl group as R may preferably be accomplished by using an aqueous alkaline metal hydroxide solution. The optional subsequent acylation can be carried out in a manner known per se.

The $\Delta^{14}$-16α,17-dihydroxypregnane derivatives of formula (I)

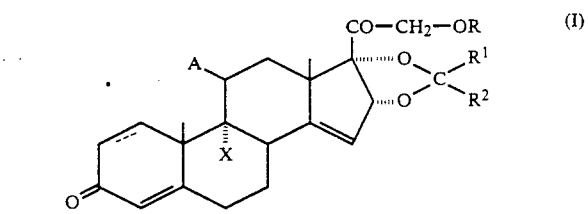

according to the invention possess valuable glucocorticoid effects.

Two principal (essential) demands are set up against topically used steroid antiinflammatory drugs: a) they should be as active as possible in various animal experiments used for investigating the antiinflammatory action; and b) they should induce the lowest harmful systemic side effect. This latter effect can be well characterized by the thymus weight-decreasing action (involution). The possibly lowest toxicity (i.e. the possibly highest $LD_{50}$ value) is an essential demand for any active agent (drug) used in therapy.

The tests used for investigation of the antiinflammatory action of the compounds according to the invention are described hereinafter. Budesonide was used as reference drug in these tests.

1) Comparative study on the acute toxicity

Animal groups consisting of 10 CFLP mice or RG Hann Wistar rats each of both sexes were used. The doses causing the death of 50% of the animals ($LD_{50}$ values) within a 2-week observation period following subcutaneous (s.c.) or oral (p.o.) administration were determined.

2) The croton oil-induced contact dermatitis model

[Endocrinology 77, 625 (1965); Toxicol. Appl. Pharmacol, 20, 552 (1971)].

Infantile female rats weighing 45 to 55 g were used. Animals had previously been selected for this test, the ear weight of which increased at least by 100% under effect of a treatment with 2% croton oil.

The test compounds were dissolved in a 2% croton oil mixture in various concentrations and then applied onto the ears of the animals. The control group was treated only with the croton oil inducing inflammation. Six hours after treatment the ears of the animals were cut off and weighed. For evaluation, the diminution of the ear weight increase was expressed as "percentage of inhibition", in comparison to the control treated with croton oil only. In the 48th hour the thymi of the animals were excised and the harmful systemic side effect of the test compounds was evaluated by comparing their thymus weight to that of the control animals.

3) The local granuloma sac model

[Recent Progr. Hormone Res. 8, 117 (1953); Arzneim.-Forsch. 27, 11 (1977)].

This method was used to investigate the antiexudative action of the topically administered glucocorticoids.

Groups consisting of 10 female RG Hann Wistar rats each weighing 130 to 150 g were used. After shaving the back of the animals 25 ml of air were injected beneath the back skin and 1 ml of 2% croton oil inducing inflammation was introduced to the air sac. After 5 days the content of the sac was removed by suction and once 3 doses each of the glucocorticoids to be tested or budesonide respectively, in a volume of 0.5 ml suspension in Tween 80 were administered by an injection syringe. On the 10th day following the start of the experiment the animals were sacrificed and the exudate liquid of the sac (expressed as ml) was measured. The percentage of the antiinflammatory effect was calculated based on the decrease in the volume of exudate related to that of the control.

Then, the thymi of the animals were excised and the harmful systemic side effect of the test compounds was calculated as a percentage based on the comparison of the thymus weight of animals treated with the test compounds to that of the untreated control group.

4) The experimental asthma model

[Br. J. Pharmac. 76, 139 (1982)]

This test was used to investigate the antiasthmatic effect of the test compounds.

It is known that by ovalbumin (OA) treatment an experimental asthma can be induced on guinea-pigs which is accompanied by dyspnoea and causes the death of the animals in severe cases. This test is useful to detect an eventual antiasthmatic effect of the test compounds.

Guinea-pigs of both sexes weighing 300 to 400 g each were used. The experimental animals were sensitized by i.p. ovalbumin (10/μg of OA+100 mg of aluminum hydroxide/animal) and after 30 days they were provoked by the intravenous (i.v.) administration of 100 mg/kg of OA. Both the test compounds and budesonide used as reference substance were given 50 mg/kg i.p. dose 20 hours before the provocation. The percentage occurrence of dyspnoea and the survival were observed.

The above investigations gave the following results ("N" means the number of animals within one group).

| | | | (1) Comparative acute toxicity | | |
|---|---|---|---|---|---|
| Species | Sex | Route of admin. | Budesonide $LD_{50}$ (mg/kg) | Compound of Ex. No. 2 $LD_{50}$ (mg/kg) | Compound of Ex. No. 6 $LD_{50}$ (mg/kg) |
| Mouse | male | s.c. | 131.08 | 584.89 | 332.82 |
| Mouse | male | p.o. | 1078.82 | >4000 | 2926.07 |
| Mouse | female | s.c. | 109.18 | 823.14 | 634.49 |
| Mouse | female | p.o. | 1356.57 | >4000 | 2789.21 |
| Rat | male | s.c. | 59.44 | 1208.94 | 161.52 |
| Rat | male | p.o. | 3395.89 | >4000 | >4000 |
| Rat | female | s.c. | 71.50 | 842.60 | 163.53 |
| Rat | female | p.o. | 2106.22 | >3000 | >3000 |

| | (2) Croton oil-induced contact dermatitis | | | | |
|---|---|---|---|---|---|
| Compound | Concentration (μg/ml) | N | Ear weight (mg) | Inhibition (%) | Relative activity | Thymus involution (%) |
| Untreated | 0 | 58 | 76.82 ± 1.1 | — | — | — |

| (2) Croton oil-induced contact dermatitis | | | | | |
|---|---|---|---|---|---|
| Compound | Concentration (μg/ml) | N | Ear weight (mg) | Inhibition (%) | Relative activity | Thymus involution (%) |
| Provoked control | 0 | 58 | 161.08 ± 2.3 | — | — | — |
| Budesonide | 1 | 28 | 144.71 ± 2.0 | 19.43 | | 9.2 |
| Budesonide | 10 | 28 | 127.78 ± 2.0 | 39.53 | 100 | 3.9 |
| Budesonide | 100 | 28 | 117.07 ± 2.7 | 52.24 | | 26.1 |
| Ex. No. 2 | 1 | 20 | 144.60 ± 2.8 | 19.56 | | 0 |
| Ex. No. 2 | 10 | 20 | 131.10 ± 2.7 | 35.59 | 78 | 0 |
| Ex. No. 2 | 100 | 20 | 118.20 ± 2.2 | 50.90 | | 9.8 |
| Ex. No. 6 | 1 | 20 | 144.40 ± 3.5 | 19.80 | | 0 |
| Ex. No. 6 | 10 | 20 | 126.90 ± 2.7 | 40.57 | 118 | 1.7 |
| Ex. No. 6 | 100 | 20 | 115.10 ± 2.6 | 54.57 | | 0 |

| (3) Antiinflammatory effect on the local granuloma sac model | | | | | |
|---|---|---|---|---|---|
| Compound | Dose (μg/sac) | N | Exudate (ml) | Inhibition (%) | Relative activity | Thymus involution (%) |
| Control | 0 | 82 | 12.73 ± 0.4 | — | — | — |
| Budesonide | 0.22 | 18 | 6.38 ± 0.4 | 49.89 | | 0 |
| Budesonide | 2.00 | 19 | 4.00 ± 0.3 | 68.58 | 100 | 0 |
| Budesonide | 18.00 | 19 | 1.84 ± 0.5 | 85.55 | | 24.43 |
| Ex. No. 2 | 0.22 | 18 | 7.47 ± 0.5 | 41.32 | | 0 |
| Ex. No. 2 | 2.00 | 19 | 5.10 ± 0.4 | 59.94 | 62 | 0 |
| Ex. No. 2 | 18.00 | 18 | 1.36 ± 0.2 | 89.32 | | 0 |
| Ex. No. 6 | 0.22 | 17 | 6.52 ± 0.6 | 48.79 | | 4.98 |
| Ex. No. 6 | 2.00 | 18 | 5.08 ± 0.4 | 60.10 | 71 | 4.98 |
| Ex. No. 6 | 18.00 | 18 | 1.69 ± 0.3 | 86.73 | | 6.22 |

| (4) The experimental asthma model | | |
|---|---|---|
| Compound | Dyspnoea (%) | Survival (%) |
| Control | 33 | 66 |
| Budesonide | 20 | 60 |
| Ex. No. 2 | 14 | 43 |
| Ex. No. 6 | 0 | 100 |

It is unambiguously evident from the results of the above investigations that the novel $\Delta^{14}$-16α,17-dihydroxypregnane derivatives of formula (I)

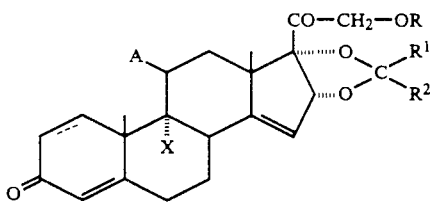

according to the invention exert a highly significant local (topical) antiinflammatory and antiasthmatic effect approaching that of the reference drug and both their harmful systemic effect (thymus involution) and toxicity are lower than those of budesonide.

The invention is illustrated in detail by the following non limiting Examples. The ratios defined for the solvent mixtures mean volume ratios.

EXAMPLE 1

Preparation of 11β,16α,17.21-tetrahydroxypregna-4,14-dien-3,20-dion-16,17-cyclic butyraldehyde acetal 0,4 g (0.951 mmol) of 11β,16α,17,21-tetrahydroxypregna-4,14-dien-3,20-dion-21-acetate is dissolved in a mixture containing 0.17 ml (1.90 mmol) of butyraldehyde, 8 ml of acetonitrile and 0.17 ml of 70% perchloric acid. Both the weighing-in and the reaction are carried out under nitrogen. After 10 minutes 4 ml of 5% potassium hydrogen carbonate solution are added to the reaction mixture and the neutralized solution is extracted with ethyl acetate. After drying the extract is evaporated under reduced pressure. The oily evaporation residue is dissolved in 6 ml of methanol under nitrogen and after adding 0.4 ml of 60% aqueous perchloric acid it is left to stand at room temperature for 10 hours. The mixture is poured into 200 ml of water, the crude product is obtained is first recrystallized from a mixture of dichloromethane and n-hexane and then from anhydrous ethanol to obtain 0.35 g (85%) of the title compound.

According to the HPLC (high performance liquid chromatography) analysis the purity of the above product is 98%, m.p.: 96°–101° C.

EXAMPLE 2

Preparation of 11β,16α,17,21-tetrahydroxypregna-1,4,14-trien-3,20-dion-16,17-cyclic butyraldehyde acetal After weighing in 3.5 ml of 70% perchloric acid and 3.5 ml of redistilled butyraldehyde into 160 ml of acetonitrile under dry nitrogen, 8.00 g (0.0191 mol) of 11β,16α,17,21-tetrahydroxypregna-1,4,14-trien-3,20-dion-21-acetate are portionwise added under stirring over 10 minutes. The steroid substance is immediately dissolved. After stirring the solution at room temperature for 30 minutes (the progress of the reaction is observed by using TLC analysis). The reaction mixture is poured into 80 ml of 5% potassium hydrogen carbonate solution and then extracted with 80 ml of ethyl acetate. After washing the extract with water up to neutral and then shaking with concentrated sodium chloride solution it is dried over anhydrous sodium sulfate and evaporated under reduced pressure until it becomes free from the solvent.

After dissolving the evaporation residue in 120 ml of methanol under nitrogen 8 ml of 70% aqueous perchloric acid are dropwise added to the solution. The reaction mixture is stirred at room temperature for 8 hours and then poured into 1600 ml of water. After stirring for 1 hour it is filtered to give 7.95 g (96.59%) of the title compound. This product is purified by suspending in 20 volumes of a 1:5 dichloromethane/n-hexane mixture and recrystallizing from a 1:4 mixture of ethanol and water. In this way a pure title compound is obtained, m.p.: 131°–134° C. (decomposition at 205° C. $/\alpha/_D^{20} = +0.69°$ (dichloromethane, c=1).

IR spectrum ($v$,cm$^{-1}$): 3420 (—OH), 1722 (20-oxo). 1657 (3-oxo), 1614 and 1598 (C=C).

EXAMPLE 3

Preparation of
11$\beta$,16$\alpha$,17,21-tetrahydroxypregna-1,4,14-trien-3,20-dion-16,17-cyclic butyraldehyde acetal 0.5 ml of 70% perchloric acid and 0.5 ml of redistilled butyraldehyde are added to 20 ml of acetonitrile under dry nitrogen, then 1.00 g of 11$\beta$,16$\alpha$,17,21-tetrahydroxypregna-1,4,14-trien-3,20-dione is added in little portions over 10 minutes while stirring. The reaction proceeds within 15 minutes. Then the reaction mixture is poured into 2000 ml of water, stirred for 1 hour and filtered. The crude title product thus obtained is purified as described in the preceding Example to obtain 1.05 g (91.8%) of pure title compound, m.p.: 130°–133° C.

EXAMPLE 4

Preparation of
11$\beta$,16$\alpha$,17,21-tetrahydroxypregna-1,4,14-trien-3,20-dion-16,17-cyclic acetaldehyde acetal After introducing 2.2 ml of 70% perchloric acid and 1.3 ml of acetaldehyde into 100 ml of acetonitrile under dry nitrogen, 5.00 g of 11$\beta$,16$\alpha$,17,21-tetrahydroxypregna-1,4,14-trien-3,20-dion-21-acetate are added in several little portions under stirring. The 21-acetoxy derivative of the cyclic acetal is first recovered as described in Example 1 which is then hydrolyzed to give 4.61 g (95.87%) of the title product, m.p.: 169–173° C.

EXAMPLE 5

Preparation of
11$\beta$,16$\alpha$,17,21-tetrahydroxypregna-1,4,14-trien-3,20-dion-16,17-cyclic benzaldehyde acetal After introducing 2.2 ml of 70% perchloric acid and 2.4 ml of redistilled benzaldehyde into 100 ml of acetonitrile under dry nitrogen, 5.00 g of 11$\beta$,16$\alpha$,17,21-tetrahydroxypregna-1,4,14-trien-3,20-dion-21-acetate are added in several little portions under stirring. The 21-acetoxy derivative of the cyclic acetal is first recovered as described in Example 1 which is then hydrolyzed to obtain 4.92 g (90.99%) of the title compound, m.p.: 228°–233° C.

EXAMPLE 6

Preparation of
11$\beta$,16$\alpha$,17,21-tetrahydroxypregna-1,4,14-trien-3,20-dion-16,17-cyclic isobutyraldehyde acetal 5.0 g of 11$\beta$,16$\alpha$,17,21-tetrahydroxypregna-1,4,14-trien-3,20-dion-21-acetate are dissolved in a mixture containing 100 ml of acetonitrile, 2.2 ml of 70% perchloric acid and 2.2 ml of isobutyraldehyde. Both the weighing-in operations and the reaction are carried out under nitrogen.

The 21-acetoxy derivative of the cyclic acetal is first recovered as described in Example 1, then the 21-acetoxy group is hydrolyzed to result in the free hydroxyl group by using aqueous perchloric acid solution to give 4.97 g (96.68%) of the title compound, m.p.: 132°–136° C., $/\alpha/_D^{24} = +0.607°$ (dichloromethane, c=1). IR spectrum ($v$, cm$^{-1}$): 3416 (—OH), 1720 (20-oxo), 1657 (3-oxo), 1618 and 1588.

EXAMPLE 7

Preparation of
11$\beta$,16$\alpha$,17,21-tetrahydroxypregna-1,4,14-trien-3,20-dion-16,17-cyclic acetonide 21-acetate 10 g (0.0239 mol) of 11$\beta$,16$\alpha$,17,21-tetrahydroxypregna-1,4,14-trien-3,20-dion-21-acetate are transformed to a paste with 125 ml of acetone under dry nitrogen at room temperature while stirring. Parallelly, 1.6 ml of concentrated sulfuric acid are slowly dropped to 1.0 ml of 70% aqueous perchloric acid under cooling and stirring in an other flask. The anhydrous perchloric acid thus prepared is added to the suspension of the steroid in acetone. The steroid is dissolved within about 10 minutes. After stirring for 2 hours the solution is poured into 1000 ml of 2% sodium hydrogen carbonate solution, stirred for 1 hour and then the precipitate is recrystallized from acetone to result in 10.01 g (91.41%) of the title compound, m.p.: 249°–261° C.

EXAMPLE 8

Preparation of
11$\beta$,16$\alpha$,17,21-tetrahydroxypregna-1,4,14-trien-3,20-dion-16,17-cyclic acetonide 2 g (0.0053 mol) of 11$\beta$,16$\alpha$,17,21-tetrahydroxypregna-1,4,14-trien-3,20-dione are transformed to a paste with 20 ml of acetone under dry nitrogen at room temperature while stirring. To this mixture 1.0 ml of 70% aqueous perchloric acid is added at room temperature under stirring. The reaction proceeds within 30 minutes. After pouring the reaction mixture into 1000 ml of 2% aqueous potassium hydrogen carbonate solution and stirring for 30 minutes, the precipitate is filtered and dried to obtain 2.02 g (91.29%) of the title substance which is recrystallized from acetone, m.p.: 212°–216° C.

EXAMPLE 9

Preparation of
11$\beta$,16$\alpha$,17,21-tetrahydroxypregna-1,4,14-trien-3,20-dion-16,17-cyclic acetonide 1.0 g (00218 mol) of 11$\beta$,16$\alpha$,17,21-tetrahydroxypregna-1,4,14-trien-3,20-dion-16,17-cyclic acetonide 21-acetate is transformed to a paste with 100 ml of methanol under nitrogen. To this mixture 0.166 g of potassium carbonate dissolved in 1.1 ml of deionized water is added. The solid phase goes into solution within 5 minutes. After 10 minutes the pH value of the solution is adjusted to 6 by adding 1N hydrochloric acid then the solution is evaporated until it becomes free from solvent. The residue is thoroughly mixed with 100 ml of deionized water, filtered and dried. The product thus obtained is recrystallized from acetone to give 0.79 g (86.98%) of the title compound, m.p.: 210°–215°215° C.

EXAMPLE 10

Preparation of 11$\beta$,16$\alpha$,17,21-tetrahydroxypregna-1,4,14-trien-3,20-dion-16,17-cyclic acetonide 1.0 g (0.00218 mol) of 11$\beta$,16$\alpha$,17,21-tetrahydroxypregna-1,4,14-trien-3,20-dion-16,17-cyclic acetonide 21-acetate is dissolved in 200 ml of methanol under nitrogen. After adding 2.0 ml of deionized water and 2.0 ml of 60% aqueous perchloric acid the reaction mixture is stirred at room temperature for 48 hours and then evaporated to one tenth of its original volume. After adding 20 ml of deionized water to the evaporation residue and extracting with dichloromethane, the extract is evaporated to dryness and the residue is recrystallized from ether to give 0.85 g (93.6%) of the title compound, 212°–216° C.

EXAMPLE 11

Preparation of 11$\beta$,16$\alpha$,17,21-tetrahydroxypregna-1,4,14-trien-3,20-dion-16,17-cyclic cyclopentanone ketal After adding 0.44 ml of 70% aqueous perchloric acid and 0.43 ml of cyclopentanone to 20 ml of acetonitrile under nitrogen, 1 g of 11$\beta$,16$\alpha$,17,21-tetrahydroxypregna-1,4,14-trien-3,20-dion-21-acetate is added to the solution at room temperature. After stirring the reaction mixture for 8 hours the 21-acetate derivative of the cyclic cyclopentanone ketal is first recovered as described in Example 1 which is then hydrolyzed according to Example 9 to obtain 0.50 g (47.3%) of the title compound, m.p.: 140°–145° C.

EXAMPLE 12

Preparation of 11$\beta$,16$\alpha$,17,21-tetrahydroxypregna-1,4,14-trien-3,20-dion-16,17-cyclic cyclohexanone ketal After adding 0.44 ml of 70% aqueous perchloric acid and 0.75 ml of cyclohexanone to 20 ml of acetonitrile under nitrogen 1 g of 11$\beta$,16$\alpha$,17,21-tetrahydroxypregna-1,4,14-trien-3,20-dion-21-acetate is added to the above solution at room temperature. After stirring the reaction mixture for 30 minutes the 21-acetate derivative of the cyclic cyclohexanone ketal is first recovered as described in Example 11 which is then hydrolyzed according to Example 9 to obtain 0.75 g (68.74%) of the title substance, m.p.: 220°–223° C.

EXAMPLE 13

Preparation of 9$\alpha$-fluoro-11$\beta$,16$\alpha$,17,21-tetrahydroxypregna-1,4,14-trien-3,20-dion-16,17-cyclic butyraldehyde acetal 0.3 g (0.69 mmol) of 9$\alpha$-fluoro-11$\beta$,16$\alpha$,17,21-tetrahydroxypregna-1,4,14-trien-3,20-dion-21-acetate is added to a mixture containing 0.13 ml of butyraldehyde, 0.14 ml of 70% aqueous perchloric acid and 30 ml of ethyl acetate. The suspension obtained becomes clear within 30 minutes. After stirring for 1 hour the reaction mixture is worked up as described in Example 1 and the 21-acetate derivative of the cyclic butyraldehyde acetal thus obtained is hydrolyzed by using 0.5 ml of 70% aqueous perchloric acid in 5 ml of methanol according to Example 9. After pouring the reaction mixture into 200 ml of water the precipitate is filtered and dried to obtain 0.24 g (77.9%) of the title compound, m.p.: 130°–136° C.

EXAMPLE 14

Preparation of 11$\beta$,16$\alpha$,17,21-tetrahydroxypregna-1,4,14-trien-3,20-dion-16,17-cyclic butyraldehyde acetal After dissolving 0.5 g (1.05 mmol) of ethyl 11$\beta$,16$\alpha$,17,21-tetrahydroxypregna-1,4,14-trien-3,20-dion-16,17-cyclic orthoformate 21-acetate in 50 ml of ethyl acetate under nitrogen, 0.19 ml of redistilled butyraldehyde and then 0.10 ml of 70% perchloric acid are added to the above solution. The suspension obtained becomes a clear solution after 2 hours. The reaction is terminated within 3 to 3.5 hours. Subsequently, the reaction mixture is washed first with 30 ml of 5% sodium hydrogen carbonate solution and then with distilled water, dried over anhydrous sodium sulfate and evaporated under reduced pressure.

The evaporation residue is dissolved in 10 ml of methanol under nitrogen at room temperature and after adding 0.6 ml of 70% aqueous perchloric acid solution, the reaction mixture is left to stand for 12 hours and then dropped into 250 ml of water. After stirring for 1 hour the suspension is filtered and the precipitate is dried. The crude product obtained is first recrystallized from a 1:5 mixture of dichloromethane/n-hexane and then from ethanol to obtain 0.30 g (66.4%) of the title substance, m.p.: 131°–134° C.

EXAMPLE 15

Preparation of 11$\beta$,16$\alpha$,17,21-tetrahydroxypregna-1,4,14-trien-3,20-dion-16,17-cyclic butyraldehyde acetal 0.19 ml of redistilled butyraldehyde and then 0.10 ml of 70% perchloric acid solution are added to 0.5 g (1.05 mmol) of methyl 11$\beta$,16$\alpha$,17,21-tetrahydroxypregna-1,4,14-trien-3,20-dion-16,17-cyclic orthoformate 21-acetate dissolved in 50 ml of ethyl acetate under nitrogen. The suspension obtained goes into solution within 2 hours. The reaction proceeds over 3 to 3.5 hours. Subsequently, the reaction mixture is washed with 30 ml of 5% sodium hydrogen carbonate solution and then with distilled water, dried over anhydrous sodium sulfate and evaporated under reduced pressure.

After dissolving the evaporation residue in 10 ml of methanol at room temperature under nitrogen, 0.6 ml of 70% aqueous perchloric acid solution is added. The reaction mixture is left to stand for 12 hours and then dropped into 250 ml of water. After stirring the suspension for 1 hour, the precipitate is filtered and dried. The crude product thus obtained is first recrystallized from a 1:5 mixture of dichloromethane/n-hexane and then from ethanol to obtain 0.33 g (70.9%) of the title compound, m.p.: 131°–134° C.

EXAMPLE 16

Preparation of 11$\beta$,16$\alpha$,17,21-tetrahydroxypregna-1,4,14-trien-3,20-dion-16,17-cyclic butyraldehyde acetal 21-butyrate 1.0 g (2.334 mmol) of 11$\beta$,16$\alpha$,17,21-tetrahydroxypregna-1,4,14-trien-3,20-dion-16,17-cyclic butyraldehyde acetal (prepared according to Example 2) is dissolved in 15 ml of anhydrous pyridine under dry nitrogen, then 0.77 ml (4.668 mmol) of butyric acid anhydride is added at room temperature. The acylation proceeds within 6 to 8 hours. Then the reaction mixture is poured into 500 ml of water containing 17 ml of concentrated hydrochloric acid, stirred for 1 hour and filtered. The prcipitate is recrystallized from ethanol and dried to obtain 1.05 g (90%) of the title product, m.p.: 123°–125° C., with an $R_f$ value of 0.50 (developed with a 70:30:2 mixture of chloroform/ether/methanol).

EXAMPLE 17

Preparation of
11β,16α,17,21-tetrahydroxypregna-1,4,14-trien-3,20-dion-16,17-cyclic butyraldehyde acetal 21-caproate 1.0 g (2.334 mmol) of 11β,16α,17,21-tetrahydroxypregna-1,4,14-trien-3,20-dion-16,17-cyclic butyraldehyde acetal (prepared according to Example 2) is dissolved in 15 ml of anhydrous pyridine under dry nitrogen and 1.08 ml of caproic acid anhydride are added at room temperature. Further on Example 16 is followed to give 1.05 g (90%) of the title compound with an $R_f$ value of 0.47 (developed with a 70:30:2 mixture of chloroform/ether/methanol).

The following examples are directed to preparing the starting materials of the Formula (II) as disclosed in commonly assigned Hungarian Patent Application 1156/89.

EXAMPLE 18

Preparation of
11β,16α,17,21-tetrahydroxypregna-4,14-dien-3,20-dion-21-acetate

A solution containing 1 g (2.588 mmol) of 11β,21-dihydroxypregna-4,16-dien-3,20-dion-21-acetate in 40 ml of glacial acetic acid is cooled to 13° to 15° C. and 0.45 g (2.847 mmol) of potassium permanganate dissolved in 40 ml of water is portionwise added at the same temperature during 5 to 10 minutes. After the addition, the excess of the oxidizing agent is decomposed by adding 0.6 g of sodium pyrosulfite dissolved in 4.0 ml of water to the reaction mixture. After stirring for 15 minutes the reaction mixture is poured into 500 ml of deionized water, stirred for 1 hour, filtered and the precipitate is washed with water up to neutral. After drying the product is recrystallized from ethyl acetate to give 0.48 g (44.3%) of the title compound, m.p.: 220°–225° C.

EXAMPLE 19

Preparation of
11β,16α,17,21-tetrahydroxypregna-1,4,14-trien-3,20-dion-21-acetate 10 g (26.0 mmol) of 11β,21-dihydroxypregna-1,4,16-trien-3,20-dion-21-acetate are dissolved in 400 ml of glacial acetic acid at 15° C., then 4.52 g (28.6 mmol) of potassium permanganate dissolved in 400 ml of water are portionwise added at the same temperature over 5 to 10 minutes. Thereafter, the excess of permanganate is decomposed by adding 5.94 g of sodium pyrosulfite dissolved in 40 ml of water. After stirring for 20 minutes the reaction mixture is poured into 10 liters of water. After stirring for 1 hour the suspension is filtered, washed up to neutral and dried. The crude product obtained is recrystallized from ethyl acetate to give 5.11 g (47.2%) of the title substance, m.p.: 238°–243° C.

EXAMPLE 20

Preparation of
11β,16α,17,21-tetrahydroxypregna-1,4,14-trien-3,20-dion-21-acetate After dissolving 55 g (143.1 mmol) of 11β, 21-dihydroxypregna-1,4,16-trien-3,20-dion-21-acetate in 1100 ml of glacial acetic acid, 1650 ml of acetone are added and the solution is cooled between −20° C. and −25° C.

20.35 g (128.8 mmol) of potassium permanganate are dissolved in 440 ml of water, cooled to 0° C. and portionwise added to the above solution of the steroid maintained at −25° C. over 10 to 15 minutes. After 5 minutes the reaction mixture is examined by thin layer chromatography [DC Alufolien Kielelgel 60 $F_{254}$ (Merck) by using a developing system containing chloroform/ether/methanol in 70:30:2 volume ratio and detecting with phosphoric acid]. After about 15 minutes no starting material can be detected in the reaction mixture. The mixture is poured into a solution containing 27 g of sodium pyrosulfite in 27.5 litres of ice-water under stirring. The suspension obtained is stirred at 0° C. for 1 hour, then filtered. The precipitate is washed up to neutral, dried and recrystallized from ethyl acetate to give 36.14 g (60.7%) of the title compound, m.p.: 240°–243° C.

EXAMPLE 21

Preparation of
11β,16α,17,21-tetrahydroxypregna-1,4,14-trien-3,20-dione 0.40 g (2.87 mmol) of potassium carbonate dissolved in 6 ml of water is added to a solution of 2 g (4.78 mmol) of 11β,16α,17,21-tetrahydroxypregna-1,4,14-trien-3,20-dion-21-acetate in 400 ml of methanol under nitrogen. After 15 minutes the pH value of the solution is adjusted to 6.5 by adding acetic acid, the mixture is evaporated to a volume of 15 to 20 ml under reduced pressure and the residue is poured into 500 ml of ice-water. After stirring for 30 minutes the suspension is filtered and the precipitate is dried. The crude product obtained is recrystallized from an 1:3 (volume ratio) mixture of chloroform/methanol to obtain 1.2 g (66.7%) of the title compound, m.p.: 240°–242° C.

EXAMPLE 22

Preparation of
16α,17,21-trihydroxypregna-4,14-dien-3,20-dion-21-acetate 0.53 g (3.373 mmol) of potassium permanganate dissolved in 5 ml of water is portionwise added at 20° C. over 5 minutes to a solution containing 1 g (2.699 mmol) of 21-hydroxypregna-4,16-dien-3,20-dion-21-acetate dissolved in 10 ml of glacial acetic acid at room temperature. After addition, the excess of permanganate is decomposed by adding a solution of 0.72 g of sodium pyrosulfite in 5 ml of water to the reaction mixture, then the mixture is poured into 500 ml of water containing 16.7 g of potassium hydrogen carbonate. After stirring for 1 hour the suspension is filtered, the precipitate is washed with water and dried to give 0.50 g (46.0%) of the title product, m.p.: 215°–220° C.

EXAMPLE 23

Preparation of
16α,17,21-trihydroxypregna-1,4,14-trien-3,20-dion-21-acetate 11 ml of acetone are added to a solution containing 0.35 g (0.95 mmol) of 21-hydroxypregna-1,4,16-trien-3,20-dion-21-acetate in 7 ml of glacial acetic acid and the solution is cooled to a temperature between −20° C. and −25° C. Thereafter, 0.23 g (1.45 mmol) of potassium permanganate dissolved in 2 ml of water is portionwise added at the same temperature. After 15 minutes the reaction mixture is poured into 200 ml of ice-water containing 0.3 g of sodium pyrosulfite. After stirring for 45 minutes the suspension is filtered, the precipitate is washed and dried to obtain 0.20 g (52.6%) of the title compound, m.p.: 220°-223° C.

EXAMPLE 24

Preparation of
9α-fluoro-11β,16α,17,21-tetrahydroxypregna-1,4,14-trien-3,20-dion-21-acetate 1.0 g (2.48 mmol) of 9α-fluoro-11β,21-dihydroxypregna-1,4,16-trien-3,20-dion-21-acetate is dissolved in 20 ml of glacial acetic acid, 30 ml of acetone are added, then the solution is cooled to a temperature between −20° C. and −25° C. A solution containing 0.36 g (2.28 mmol) of potassium permanganate in 10 ml of water is portionwise added at the same temperature. After 20 minutes the reaction mixture is poured into 500 ml of ice-water containing 0.5 g of sodium pyrosulfite. After stirring for 1 hour the suspension is filtered, the precipitate is washed with cold water and dried to give 0.79 g (73.2%) of the title compound, m.p.: 242°-247° C.

EXAMPLE 25

Preparation of
11β,16α,17,21-tetrahydroxypregna-1,4,14-trien-3,20-dion-11-trifluoroacetate-21-acetate After dissolving 5 g (10.41 mmol) of 11β-trifluoroacetoxy-21-acetoxypregna-1,4,16-trien-3,20-dione in a mixture comprising 100 ml of glacial acetic acid and 150 ml of acetone the solution is cooled to a temperature between −20° C. and −25° C., then 1.48 g (9.37 mmol) of potassium permanganate dissolved in 25 ml of water are added at the same temperature. The excess of the oxidizing agent is decomposed by adding 2.0 g of sodium hydrogen sulfite dissolved in 10 ml of water, then the mixture is poured into 2500 ml of ice-water. After stirring for 1 hour the suspension is filtered, the precipitate is washed with a little volume of cold water and dried to give 3.20 g (60.0%) of the title product, m.p.: 119°-124° C.

EXAMPLE 26

Preparation of
11β,16α,17,21-tetrahydroxypregna-1,4,14-trien-3,20-dion-21-benzoate 150 ml of acetone are added to a solution containing 5 g of 11β,21-dihydroxypregna-1,4,16-trien-3,20-dion-21-benzoate in 100 ml of glacial acetic acid, the solution is cooled to a temperature between −20° C. and −25° C. and 1.59 g of potassium permanganate dissolved in 25 ml of water are added at the same temperature. The excess of the oxidizing agent is decomposed by adding 2.5 g of sodium hydrogen sulfite dissolved in 10 ml of water, then the mixture is poured into 2500 ml of ice-water. After stirring for 1 hour the suspension is filtered, the precipitate is washed with a little volume of cold acetone-water mixture and dried to obtain 3.83 g (71.5%) of the title compound, m.p.: 155°-158° C.

The following Δ$^{14}$-16α,17-dihydroxypregnane starting materials were also prepared as described in Examples 18 to 26: 11β,16α,17,21-tetrahydroxypregna-1,4,14-trien-3,20-dion-21-butyrate; and 11β,16α,17,21-tetrahydroxypregna-1,4,14-trien-3,20-dion-21-caproate.

We claim;

1. A compound of the formula (I),

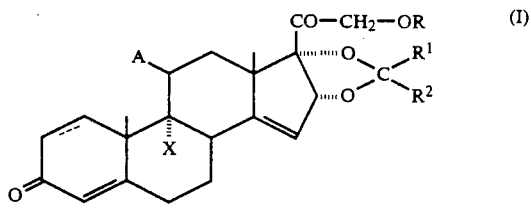

wherein
A stands for hydrogen or hydroxyl group;
X stands for hydrogen or halogen with the proviso that if A is hydrogen, then X also means hydrogen;
R stands for hydrogen, benzoyl or $C_{1-8}$alkanoyl group;
$R^1$ and $R^2$, which are the same or different, stand for hydrogen or a $C_{1-4}$alkyl group; or one of $R^1$ and $R^2$ is hydrogen and the other is phenyl group; or $R^1$ and $R^2$ together form a $C_{4-5}$alkylene group; ═ means a single or double bond between two adjacent carbon atoms.

2. A compound defined in claim 1 selected from the group consisting of
11β,16α,17,21-tetrahydroxypregna-4,14-dien-3,20-dion-16,17-cyclic butyraldehyde acetal;
11β,16α,17,21-tetrahydroxypregna-1,4,14-trien-3,20-dion-16,17-cyclic butyraldehyde acetal;
11β,16α,17,21-tetrahydroxypregna-1,4,14trien-3,20-dion-16,17-cyclic acetaldehyde acetal;
11β,16α,17,21-tetrahydroxypregna-1,4,14-trien-3,20-dion-16,17-cyclic benzaldehyde acetal;
11β,16α,17,21-tetrahydroxypregna-1,4,14-trien-3,20-dion-16,17-cyclic isobutyraldehyde acetal;
11β,16α,17,21-tetrahydroxypregna-1,4,14-trien-3,20-dion-16,17-cyclic acetonide;
11β,16α,17,21tetrahydroxypregna-1,4,14-trien-3,20-dion-16,17-cyclic cyclopentanone ketal;
11β,16α,17,21-tetrahydroxypregna-1,4,14-trien-3,20-dion-16,17-cyclic cyclohexanone ketal; and
9α-fluoro-11β,16α,17,21-tetrahydroxypregna-1,4,14-trien-3,20-dion-16,17-cyclic butyraldehyde acetal.

3. An antiinflammatory pharmaceutical composition, which comprises a therapeutically effective dose of a compound of the formula (I), wherein A, X, $R^1$, $R^2$, R and the symbol (bond line) are as defined in claim 1, in admixture with carriers and/or diluting, stabilizing, pH- and osmotic pressure-adjusting agents and formulating additives commonly used in the pharmaceutical industry.

4. Method for treating mammals suffering from an inflammatory disease, characterized by using a therapeautically effective amount of the compound of the formula (I) as defined in claim 1.

5. 11β, 16α,17,21-tetrahydroxypregna-1,4,14-triene-3,20-dione-16,17-cyclic butyraldehyde acetal as defined in claim 1.

6. 11β,16α, 17,21-tetrahydroxypregna-1,4,14-triene-3,20-dione-16,17-cyclic isobutyraldehyde acetal as defined in claim 1.

* * * * *